United States Patent [19]

Aoyama et al.

[11] Patent Number: 5,185,483
[45] Date of Patent: Feb. 9, 1993

[54] PROCESS FOR PREPARING PENTAFLUORODICHLOROPROPANES

[75] Inventors: Hirokazu Aoyama; Takashi Yasuhara; Satoru Kono; Satoshi Koyama; Souichi Ueda, all of Settsu, Japan

[73] Assignee: Daikin Industries, Ltd., Osaka, Japan

[21] Appl. No.: 812,277

[22] Filed: Dec. 23, 1991

[30] Foreign Application Priority Data

Dec. 25, 1990 [JP] Japan ................................ 2-405697

[51] Int. Cl.$^5$ ............................................. C07C 19/08
[52] U.S. Cl. ................................................. 570/172
[58] Field of Search ........................................ 570/172

[56] References Cited

U.S. PATENT DOCUMENTS 2,462,402  2/1949  Joyce ................................. 570/172

FOREIGN PATENT DOCUMENTS 9108183  6/1991  PCT Int'l Appl. ................. 570/172

OTHER PUBLICATIONS

Synthesis of Chlorofluoropropanes, Mar. 1949, pp. 979-980, vol. 71, by Coffman et al.
Collection Czechoslov. Chem. Commun., vol. 36, 1971, pp. 1867-1875, by Paleta et al., "Addition Reactions of Haloolefins. XI".

Primary Examiner—Alan Siegel
Attorney, Agent, or Firm—Birch, Stewart, Kolasch & Birch

[57] ABSTRACT

1,1,1,2,2-Pentafluoro-3,3-dichloropropane and 1,1,2,2,3-pentafluoro-1,3-dichloropropane are prepared in pure forms by reacting dichlorofluoromethane and tetrafluoroethylene, or chloroform, difluorochloromethane and tetrafluoroethylene in the presence of a catalyst comprising a halogenated zirconium of the formula:

$$ZrCl_xF_y \qquad (I)$$

wherein x and y are numbers which satisfy the relationships $x+y=4$, $0<x\leq 4$ and $0\leq y<4$.

8 Claims, No Drawings

PROCESS FOR PREPARING PENTAFLUORODICHLOROPROPANES

BACKGROUND OF THE INVENTION

1. Field of the Invention

The present invention relates to a process for preparing pentafluorodichloropropanes, in particular, 1,1,1,2,2-pentafluoro-3,3-dichloropropane (hereinafter referred to as "R-225ca") and 1,1,2,2,3-pentafluoro-1,3-dichloropropane (hereinafter referred to as "R-225cb") which are substitutes for industrially important 1,1,2-trichloro-1,2,2-trifluoroethane and have less influence on the global environment.

2. Description of the Related Art

Hitherto, R-225ca and R-225cb have been technically prepared by reacting tetrafluoroethylene (hereinafter referred to as "TFE") and dichlorofluoromethane (hereinafter referred to as "R-21") at a reaction temperature of 15 to 100° C. in the presence of a catalyst comprising anhydrous aluminum chloride (cf. U.S. Pat, No. 2,462,402, J. Amer. Chem. Soc., 71, 979, and Collect. Czechoslov. Chem. Commun., 36, 1867).

However, if TFE and R-21 are reacted in the presence of the same catalyst, namely anhydrous aluminum chloride at 0° C., 2,2-dichloro-1,1,1,3,3-pentafluoropropane (hereinafter referred to as "R-225aa") is produced (cf. Japanese Patent Kokai Publication No. 209824/1990).

From the above facts, it is highly expected that R-225aa will be by-produced when R-225ca and R-225cb are prepared by reacting TFE and R-21 in the presence of the catalyst comprising anhydrous aluminum chloride. In fact, analysis of the product of this reaction reveals that R-225aa is contained together with R-225ca and R-225cb.

Accordingly, the by-production of R-225aa is unavoidable when R-225ca and R-225cb are prepared by the above conventional process, and a yield and selectivity of the desired compounds are not increased. Therefore, the conventional process is uneconomical in the commercial scale production of R-225ca and R-225cb.

When R-225aa is removed from a mixture of R-225ca, R-225cb and R-225aa to obtain pure R-225ca or a pure mixture of R-225ca and R-225cb, rectification, which is a known purification procedure, cannot effectively and economically separate R-225aa, since R-225aa has a boiling point (51° C.) which is very close to that of R-225ca (51.1° C.).

At present, it is not certain whether or not R-225aa will be tested for its safety or other properties. Therefore, it is desirable to suppress the by-production of R-225aa as much as possible.

SUMMARY OF THE INVENTION

An object of the present invention is to provide a process for preparing R-225ca and R-225cb, which can suppress the by-production of R-225aa.

According to the present invention, there is provided a process for preparing R-225ca and R-225cb, which comprises reacting R-21 and TFE, or chloroform, difluorochloromethane (R-22) and TFE in the presence of a catalyst comprising a halogenated zirconium of the formula:

$$ZrCl_xF_y \tag{I}$$

wherein x and y are numbers which satisfy the relationships $x+y=4$, $0<x\leq4$ and $0\leq y<4$.

DETAILED DESCRIPTION OF THE INVENTION

In the process of the present invention, when R-225ca, R-225cb or a mixture thereof is used as a solvent, a predetermined amount of the catalyst is suspended in the solvent, and TFE and R-21 are supplied in the solution at a predetermined molar ratio at predetermined flow rates at a specific temperature. When chloroform, R-22 and TFE are used, a predetermined amount of the catalyst is suspended in chloroform, and TFE and R-22 are supplied in chloroform at a predetermined molar ratio at predetermined flow rates at a specific temperature. As the reaction proceeds, a reaction mixture containing increased amounts of R-225ca and R-225cb is separated from the catalyst and recovered.

The suspended catalyst can be separated from the reaction medium by a per se conventional method such as separation in a liquid state such as filtration or centrifugal sedimentation, or separation in a gas state such as evaporation.

Since the recovered reaction mixture contains no R-225aa, a mixture of R-225ca and R-225cb or pure R-225ca or R-225cb can be economically obtained after suitable separation and purification, such as rectification.

Using the catalyst of the present invention, it is possible to remove chloroform from a mixture of R-225ca, R-225cb, R-225aa, chloroform and other compounds, which mixture is obtained by reacting R-21 and TFE in the presence of any catalyst. Such removal is accomplished by suspending the catalyst in such mixture and supplying R-22 and TFE in the mixture at a predetermined molar ratio at predetermined flow rates at a specific temperature.

In the present invention, the reaction is preferably carried out by continuously supplying the raw materials and continuously recovering the products in view of economy. It is also possible to employ a semi-batchwise reaction in which certain amounts of the raw materials are charged in a reactor, reacted for a certain time and then the reaction products are recovered, or a batchwise reaction in which certain amounts of the raw materials are charged to a reactor and, after the completion of the reaction, the reaction products are recovered.

Alternatively, the reaction of the present invention can be carried out in a gas phase by filling the catalyst in a reaction tube and feeding the raw materials at predetermined flow rates.

Though the reaction of the present invention may be carried out in the absence of a solvent, it can be carried out in the presence of a solvent which is inactive to the catalyst, and in which R-21, R-22, chloroform and TFE are dissolved.

For example, the solvent may be a chloroalkane such as chloroform which is one of the raw materials for the reaction of the present invention, or hydrochlorofluoroalkanes such as tetrafluorotrichloropropanes which are byproducts in the reaction of the present invention. Further, a commonly used solvent such as dichloromethane, which is a kind of chloroalkane, or tetrachlorotetrafluoropropane or tetrachlorohexafluorobutane, which are chlorofluoroalkanes, may be used.

From the viewpoint of the reaction, chloroform is preferably used as the solvent. In view of the separation of R-225ca and R-225cb, R-225ca and R-225cb themselves are used as the solvents.

When R-21 and TFE are used as the raw materials, the molar ratio of R-21 to TFE is at least 1:1, preferably from 1:1 to 1:10.

When chloroform, R-22 and TFE are used as the raw materials, the molar ratio of chloroform to R-22 is at least 1:1, preferably from 1:1 to 1:10, and the molar ratio of R-22 to TFE is at least 1:2, preferably from 1:2 to 1:10. A molar ratio of chloroform/R-22/TFE is for example, 1:2:4.

The raw materials are premixed and then charged in the reactor, or they are separately charged in the reactor simultaneously. In some cases, R-21 is charged for a certain time period and then TFE is charged for a certain time period, or a certain amount of chloroform is charged for a certain time period and then a mixture of R-22 and TFE is charged. The raw materials can be charged in a gas state or a liquid state.

Among the catalyst of the formula (I), anhydrous zirconium chlorofluoride may be prepared by reacting anhydrous zirconium chloride with hydrogen fluoride or a fluoro or chlorofluoro-hydrocarbon having up to 4 carbon atoms, preferably 1 or 2 carbon atoms (e.g. trifluoromethane, difluoromethane, tetrafluoroethane, pentafluoroethane, chlorotrifluoromethane, dichlorodifluoromethane, trifluorochloromethane, chloropentafluoroethane, dichlorotetrafluoroethane, trifluorotrichloroethane, difluorotetrachloroethane, chlorodifluoromethane, dichlorofluoromethane, trifluorodichloroethane, trifluorochloroethane, etc.).

In the above preparation step, hydrogen fluoride, the fluorohydrocarbon or the chlorofluorohydrocarbon may be reacted alone, or it may be reacted in combination with a chlorohydrocarbon. The reaction temperature is from 0° to 120° C., preferably from 0° to 100° C. The above fluorination compound may be contacted with anhydrous zirconium chloride in the liquid state or the gas state.

Among the catalysts, anhydrous zirconium tetrachloride is commercially available.

The amount of the catalyst is not critical. Usually, 0.01 to 30% by weight, preferably 0.1 to 20% by weight of the catalyst is used based on the weight of the charged raw materials. When the solvent is used, the catalyst is used in an amount of 0.01 to 50% by weight, preferably 0.1 to 30% by weight based on the weight of the solvent.

The reaction temperature is from −30° to +120° C., preferably from −20° to +60° C. When the reaction temperature is higher than 120° C., an amount of the by-products increases so that the selectivity of desired R-225ca and R-225cb decreases. When the reaction temperature is lower than −30° C., the reaction rate becomes unpractically low.

Thje reaction pressure is not critical either. A reduced pressure may be applied. Since the reaction apparatus becomes complicated when the reduced pressure is employed, atmospheric pressure or elevated pressure is preferred.

R-21, R-22, chloroform and TFE which are the raw materials in the process of the present invention are commercially produced.

According to the present invention, R-225aa which is hardly separated by a conventional separation method is not by-produced, so that pure R-225ca and R-225cb can be economically produced.

PREFERRED EMBODIMENTS OF THE INVENTION

The present invention will be illustrated by following Examples.

EXAMPLE 1

In a 100 ml glass flask equipped with a silica gel-filled drying tube, for preventing contamination of a reaction system with water, and a gas inlet tube, 1,1,1,3-tetrachloro-2,2,3,3-tetrafluoropropane (R-214) (40 g) as a solvent and anhydrous zirconium tetrachloride (2 g) were charged.

While cooling the exterior of the flask with iced water and stirring the content with a magnetic stirrer, R-21 and TFE were premixed and supplied in the flask through the inlet tube at flow rates of 20 cc/min. and 22 cc/min., respectively. The reaction, temperature was 5° to 10° C.

After 3 hours of reaction, the amount of the reaction mixture increased by 33.9 g. According to the analysis by gas chromatography, the product had the following composition (except the solvent R-214):

| | |
|---|---|
| R-225ca | 42.8% |
| R-225cb | 52.2% |
| Chloroform | 1.5% |
| R-224ca*[1] | 1.1% |
| R-226, 223, etc.*[2] | 2.4% |

Note:
*[1] 1,1,3-Trichloro-2,2,3,3-tetrafluoropropane.
*[2] A mixture of R-226 (chlorohexapropane), R-223 (tetrachlorotrifluoropropane) and the like.

The liquid phase in column used in the gas chromatography was 25% of Octoil S (a trade mark of GL Science), and the column length was 10 m.

COMPARATIVE EXAMPLE

In the same manner as in Example 1 but using anhydrous aluminum chloride in place of anhydrous zirconium tetrachloride, the reaction was carried out. The result of the gas chromatographic analysis of the product is as follows:

| | |
|---|---|
| R-225aa | 2.5% |
| R-225ca | 51.4% |
| R-225cb | 41.1% |
| Chloroform | 1.9% |
| R-224*[1] | 1.4% |
| R-226, 223, etc. | 1.7% |

Note:
*[1] R-224 represents a mixture of trichlorotetrafluoropropane isomers.

EXAMPLE 2

In the same manner as in Example 1 but using a mixture of R-225ca and R-225cb in a weight ratio of 54/46 as a solvent, the reaction was carried out. The increase of the product weight after the reaction was 30.2 g. The result of the gas chromatographic analysis of the product is as follows:

| | |
|---|---|
| R-225ca | 46.3% |
| R-225cb | 50.1% |
| Chloroform | 1.2% |
| R-224ca | 0.9% |

-continued

| | |
|---|---|
| R-226, 223, etc. | 1.5% |

No R-225aa was detected.

EXAMPLE 3

In the same flask as used in Example 1, chloroform (40 g) and anhydrous zircorium tetrachloride (2 g) were charged. While stirring the content with a magnetic stirrer, R-22 and TFE were premixed and supplied in the flask through the inlet tube at flow rates of 20 cc/min. and 40 cc/min., respectively. The reaction temperature was 5 to 10° C.

In the course of the reaction, the reaction mixture was analyzed by the gas chromatography to reveal that the amount of chloroform decreased and amounts of R-225ca and R-225cb increased as time passed. The reaction was continued until the content of chloroform decreased to 0.1%. After the reaction, the weight of the reaction mixture was 127.4 g, and it had the following composition:

| | |
|---|---|
| R-225ca | 44.8% |
| R-225cb | 48.9% |
| Chloroform | 0.1% |
| R-224ca | 4.9% |
| R-226, 223, etc. | 1.3% |

No R-225aa was detected.

EXAMPLE 4

In a SUS 316 made 100 ml autoclave, anhydrous zirconium tetrachloride (4 g) was charged and cooled with dry ice. R-21 (30.9 g) was supplied in the liquid state and stirring was started. Then, TFE was injected to the internal pressure of 8 kg/cm²G at a reaction temperature of to 10° C. As the reaction proceeded, the internal pressure decreased. When the internal pressure dropped to 6 kg/cm²G, TFE was again injected to increase the internal pressure to kg/cm²G. The reaction was continued with repeating the above steps till no pressure drop was detected. After removing unreacted TFE from the autoclave, the reaction mixture was recovered. The amount of the reaction mixture was 57.9 g, and it had the following composition:

| | |
|---|---|
| R-225ca | 43.7% |
| R-225cb | 47.3% |
| Chloroform | 6.8% |
| R-224ca | 1.9% |
| R-226, 223, etc. | 0.3% |

No R-225aa was detected.

Example 5

Anhydrous zirconium tetrachloride (20 g) and fluorotrichloromethane (20 g) were mixed and stirred at 0° to 20° C. for 2 hours. Then, the solvent was evaporated off under reduced pressure to obtain anhydrous zirconium chlorofluoride. In the same manner as in Example 1 but using this zirconium chlorofluoride in place of anhydrous zirconium tetrachloride, the reaction was carried out. The composition of the product was follows:

| | |
|---|---|
| R-225ca | 40.9% |
| R-225cb | 54.8% |
| Chloroform | 1.1% |
| R-224ca | 0.9% |
| R-226, 223, etc. | 2.3% |

No R-225aa was detected.

EXAMPLE 6

In a 100 ml three-necked flask equipped with a silica gel-filled drying tube, a mixture of R-225ca and R-225cb (in a molar ratio of 92:8) containing 3% by mole of chloroform (40 g) was charged. After charging anhydrous zirconium tetrachloride (2 g), R-22 and TFE were premixed and supplied to the flask at flow rates of 10 cc/min. and 30 cc/min., respectively. The reaction temperature was 5° to 10° C.

After 6 hours of reaction, a concentration of chloroform in the mixture of R-225ca and R-225cb was decreased to 0.8% by mole.

What is claimed is:

1. A process for preparing 1,1,1,2,2-pentafluoro-3,3-dichloropropane and 1,1,2,2,3-pentafluoro-1,3-dichloro-225cb propane, which comprises reacting dichlorofluoromethane and tetrafluoroethylene, or chloroform, difluorochloromethane and tetrafluoroethylene in the presence of a catalyst comprising a halogenated zirconium of the formula:

$$ZrCl_xF_y \qquad (1)$$

wherein x and y are numbers which satisfy the relationships $x+y=4$, $0<x \leq 4$ and $0 \leq y<4$.

2. The process according to claim 1, wherein said halogenated zirconium is zirconium tetrachloride.

3. The process according to claim 1, wherein the amount of said catalyst is from 0.01 to 30% by weight based on the weight of raw materials.

4. The process according to claim 1, wherein the reaction temperature is from $-30°$ to $+120°$ C.

5. The process according to claim 1, wherein said reaction is carried out in the presence of a solvent which dissolves said dichlorofluoromethane, difluorochloromethane, tetrafluoroethylene, and chloroform, and which is inactive to said catalyst.

6. The process according to claim 5, wherein said solvent is a chloroalkane, a chlorofluoroalkane or a hydrochlorofluoroalkane.

7. The process according to claim 1, wherein dichlorofluoromethane and tetrafluoroethylene are used as starting materials, and the molar ratio of dichlorofluoromethane to tetrafluoroethylene is at least 1:1.

8. The process according to claim 1, wherein chloroform, difluorochloromethane, and tetrafluoroethylene are used as starting materials, and the molar ratio of chloroform to difluorochloromethane is at least 1:1 and the molar ratio of difluorochloromethane to tetrafluoroethylene is at least 1:2.

* * * * *